(12) United States Patent
Sakurada (10) Patent No.: US 9,320,425 B2
(45) Date of Patent: Apr. 26, 2016

(54) SUBJECTIVE OPTOMETER

(71) Applicant: KABUSHIKI KAISHA TOPCON, Itabashi-ku (JP)

(72) Inventor: Tomohiro Sakurada, Itabashi-ku (JP)

(73) Assignee: KABUSHIKI KAISHA TOPCON, Itabashi-ku (JP)

(*) Notice: Subject to any disclaimer, the term of this patent is extended or adjusted under 35 U.S.C. 154(b) by 0 days.

(21) Appl. No.: 14/403,253

(22) PCT Filed: May 30, 2013

(86) PCT No.: PCT/JP2013/065077
§ 371 (c)(1),
(2) Date: Nov. 24, 2014

(87) PCT Pub. No.: WO2014/013801
PCT Pub. Date: Jan. 23, 2014

(65) Prior Publication Data
US 2015/0157201 A1 Jun. 11, 2015

(30) Foreign Application Priority Data
Jul. 18, 2012 (JP) .................. 2012-159777

(51) Int. Cl.
*A61B 3/02* (2006.01)
*A61B 3/14* (2006.01)
(Continued)

(52) U.S. Cl.
CPC .............. *A61B 3/0285* (2013.01); *A61B 3/028* (2013.01); *A61B 3/09* (2013.01)

(58) Field of Classification Search
USPC ................................. 351/200–246
See application file for complete search history.

(56) References Cited

U.S. PATENT DOCUMENTS

| | | | | |
|---|---|---|---|---|
| 5,237,351 | A * | 8/1993 | Kohayakawa | A61B 3/103 351/237 |
| 6,715,877 | B2 * | 4/2004 | Molebny | A61B 3/1015 351/211 |
| 8,622,547 | B2 * | 1/2014 | Hayashi | A61B 3/102 351/206 |

(Continued)

FOREIGN PATENT DOCUMENTS

| | | |
|---|---|---|
| JP | 05-076496 A | 3/1993 |
| JP | 06-277181 A | 10/1994 |

(Continued)

OTHER PUBLICATIONS

International Search Report issued Jul. 2, 2013 in PCT/JP2013/065077 filed May 30, 2013.

*Primary Examiner* — Mohammed Hasan
(74) *Attorney, Agent, or Firm* — Oblon, McClelland, Maier & Neustadt, L.L.P.

(57) ABSTRACT

A subjective optomater that is capable of measuring accommodation ability of an eye while reducing the influence of accommodative convergence is provided. A subjective optometer includes: a visual target that is presented to an eye through a measuring optical axis; a measuring optical system that includes a spherical lens capable of changing spherical power on the measuring optical axis; a spherical power changer that changes the spherical power of the spherical lens; and an optical axis deflector that deflects the measuring optical axis so as to align the measuring optical axis with a visual axis of the eye, wherein accommodation ability is measured based on the spherical power of the spherical lens in a state in which the measuring optical axis is deflected by the optical axis deflector.

5 Claims, 9 Drawing Sheets

(51) Int. Cl.
 *A61B 3/028* (2006.01)
 *A61B 3/09* (2006.01)

(56) References Cited

U.S. PATENT DOCUMENTS

2005/0018132 A1 1/2005 Fukuma et al.
2005/0174536 A1 8/2005 Hanaki et al.

FOREIGN PATENT DOCUMENTS

| JP | 11-113848 A | 4/1999 |
| JP | 2005-177357 A | 7/2005 |
| JP | 2008-148930 A | 7/2008 |
| WO | 03/041571 A1 | 5/2003 |

* cited by examiner

SUBJECTIVE OPTOMETER

TECHNICAL FIELD

The present invention relates to a subjective optometer.

BACKGROUND TECHNOLOGY

A subjective optometer is an apparatus that presents visual targets (eye charts) to an eye and examines visual functions of the eye based on responses regarding visual performance from a subject.

A human eye has a function that tries to obtain a clear vision of a visual target (that is, tries to focus on the visual target) by adjusting thickness of a crystalline lens. The degree of this visual function is accommodation ability. In an accommodation ability test for measuring accommodation ability by using a subjective optometer, an accommodation ability test is carried out by means of spherical lenses. This method presents visual targets to an eye, sequentially varies spherical powers of the spherical lenses arranged on measuring optical axis, and measures accommodation ability of the eye based on the spherical power applied when the eye becomes incapable of focusing on the visual targets (that is, when the subject answers that he cannot see the visual targets clearly).

PRIOR ART DOCUMENT

Patent Document

[Patent Document 1] Japanese Laid-open Patent Publication No. 2008-148930

SUMMARY OF THE INVENTION

Problem to be Solved by the Invention

When accommodation occurs for thickening crystalline lenses, human eyes cause convergence of visual axes (convergence of visual axes or optic axes is simply referred to as "convergence" in the present specification) (that is, human eyes become crossed-eye). The convergence occurs automatically for the subject and is a phenomenon referred to as accommodative convergence in this technical field. In the abovementioned accommodation ability test by means of spherical lenses, accommodative convergence occurs from accommodation of eyes in response to spherical powers of spherical lenses. Then, a difference between a measuring optical axis and a visual axis is caused from the accommodative convergence, and a situation occurs in which it becomes difficult for the eyes to fuse a visual target from this difference. Therefore, when a subject has answered that a visual target cannot be seen clearly, accommodation ability test by means of a conventional subjective optomater cannot determine whether this answer is obtained from lack of accommodation ability of the eyes or lack of fusion caused by accommodative convergence. In other words, a conventional subjective optomater has a problem that is not capable of measuring the accommodation ability of the eyes with preferable accuracy on account of influence of accommodative convergence.

The present invention has been accomplished for the purpose of solving the abovementioned problem and the objective thereof is to provide a subjective optomater that is capable of measuring accommodation ability of an eye while reducing the influence of accommodative convergence.

Means for Solving the Problem

The invention of claim 1 is a subjective optometer comprising: a visual target that is presented to an eye through a measuring optical axis; a measuring optical system that includes a spherical lens capable of changing spherical power on the measuring optical axis; a spherical power changer that changes the spherical power of the spherical lens; and an optical axis deflector that deflects the measuring optical axis so as to align the measuring optical axis with a visual axis of the eye, wherein accommodation ability is measured based on the spherical power of the spherical lens in a state in which the measuring optical axis is deflected by the optical axis deflector.

The invention of claim 2 is the subjective optometer of claim 1, wherein the optical axis deflector includes prism lenses that deflects the measuring optical axis to align the measuring optical axis with the visual axis.

The invention of claim 3 is the subjective optometer of claim 2, further comprising a deflection controller that obtains a deflection angle of the measuring optical axis based on the spherical power of the spherical lens and selects a prism lens corresponding to the deflection angle obtained.

The invention of claim 4 is the subjective optometer of claim 1, comprising a visual target optical system for each of a right and left eyes in which the visual target and the measuring optical system are integrally configured, wherein the visual target optical system is capable of being driven, wherein the optical axis deflector includes a driver that drives the visual target optical system.

The invention of claim 5 is the subjective optometer of claim 4, further comprising a deflection controller that obtains a deflection angle of the measuring optical axis based on the spherical power of the spherical lens and controls the optical axis deflector to drive the visual target optical system based on the deflection angle obtained.

Effect of the Invention

A subjective optomater according to the present invention is capable of measuring accommodation ability of an eye with preferable accuracy by reducing the influence of accommodative convergence.

MODES FOR CARRYING OUT THE INVENTION

Examples of embodiments of subjective optomaters according to the present invention are explained with reference to drawings.

First Embodiment

[Configuration]

Figure 1:
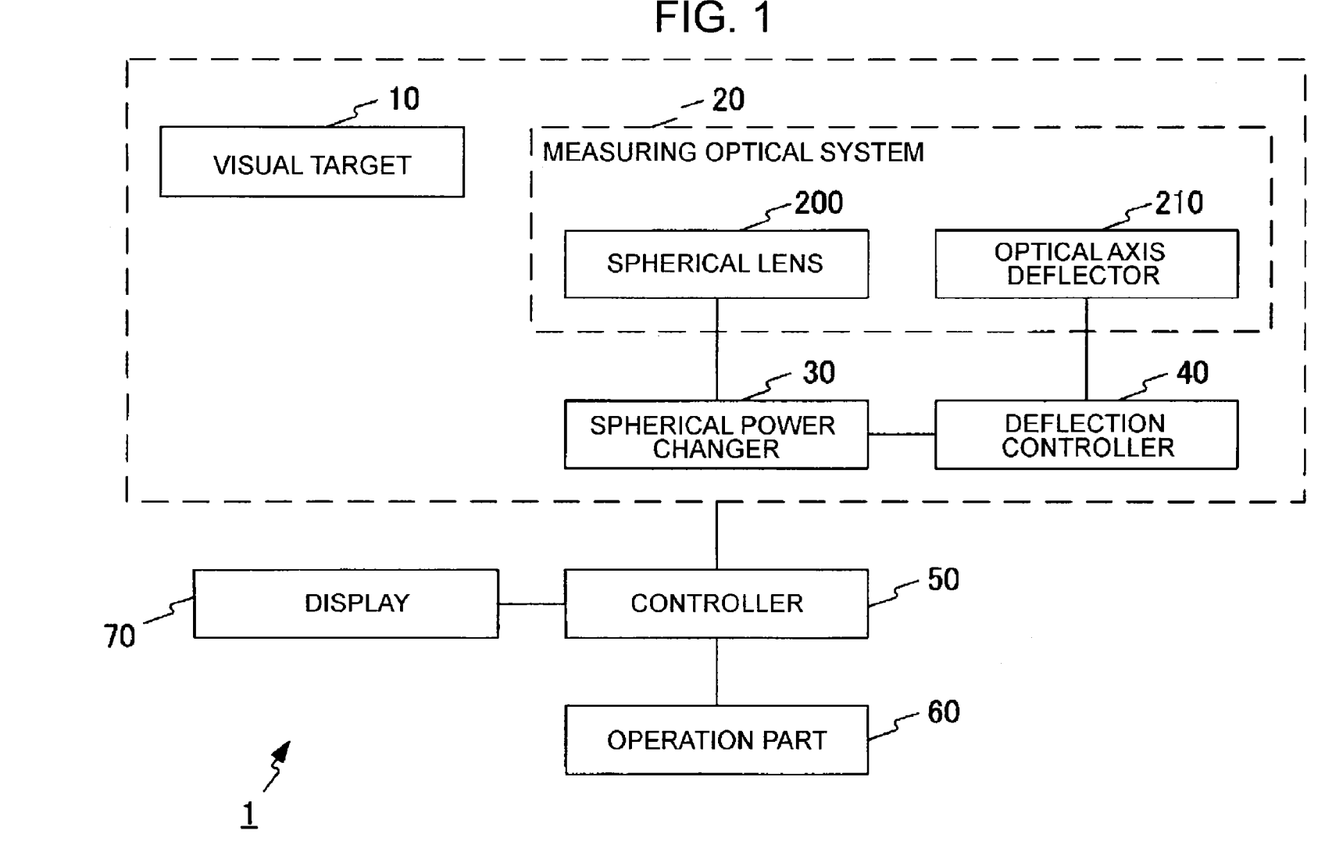
FIG. 1 is a block diagram illustrating an example of a configuration of a subjective optomater according to an embodiment.
Figure 2:
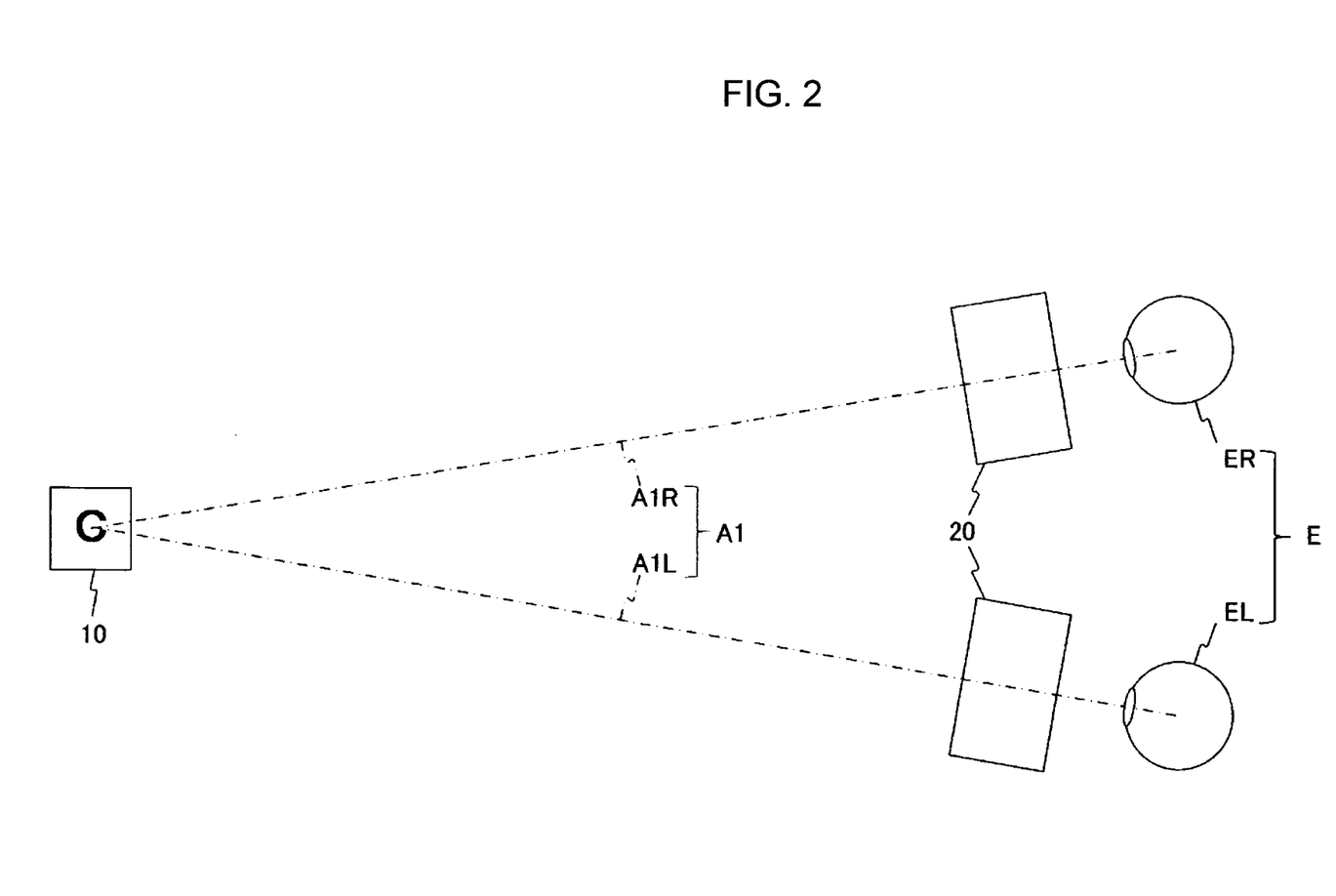
FIG. 2 is a schematic diagram illustrating an outline of a subjective optomater according to an embodiment.
Figure 3:
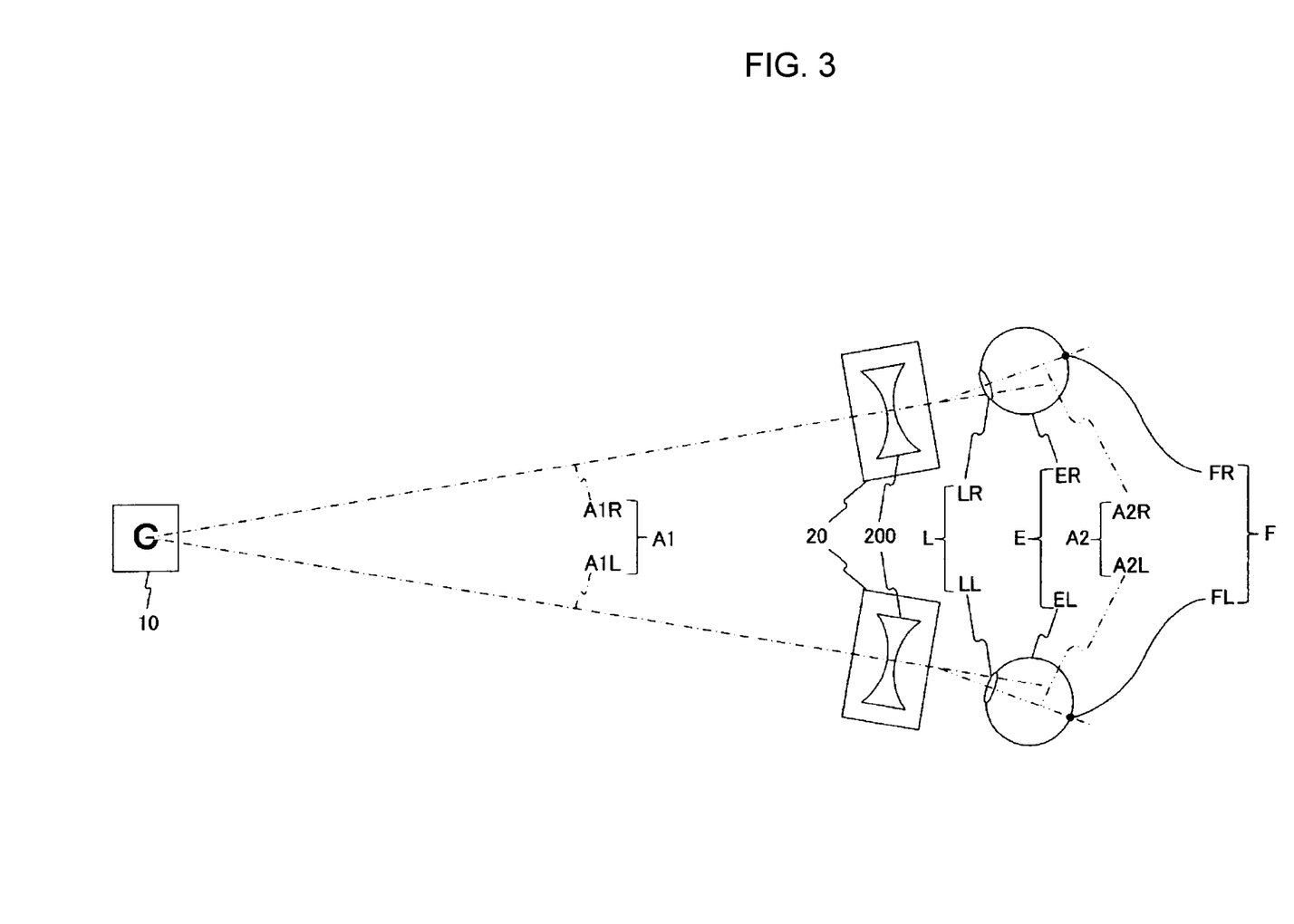
FIG. 3 is a schematic diagram illustrating an outline of a subjective optomater according to an embodiment.
Figure 4:
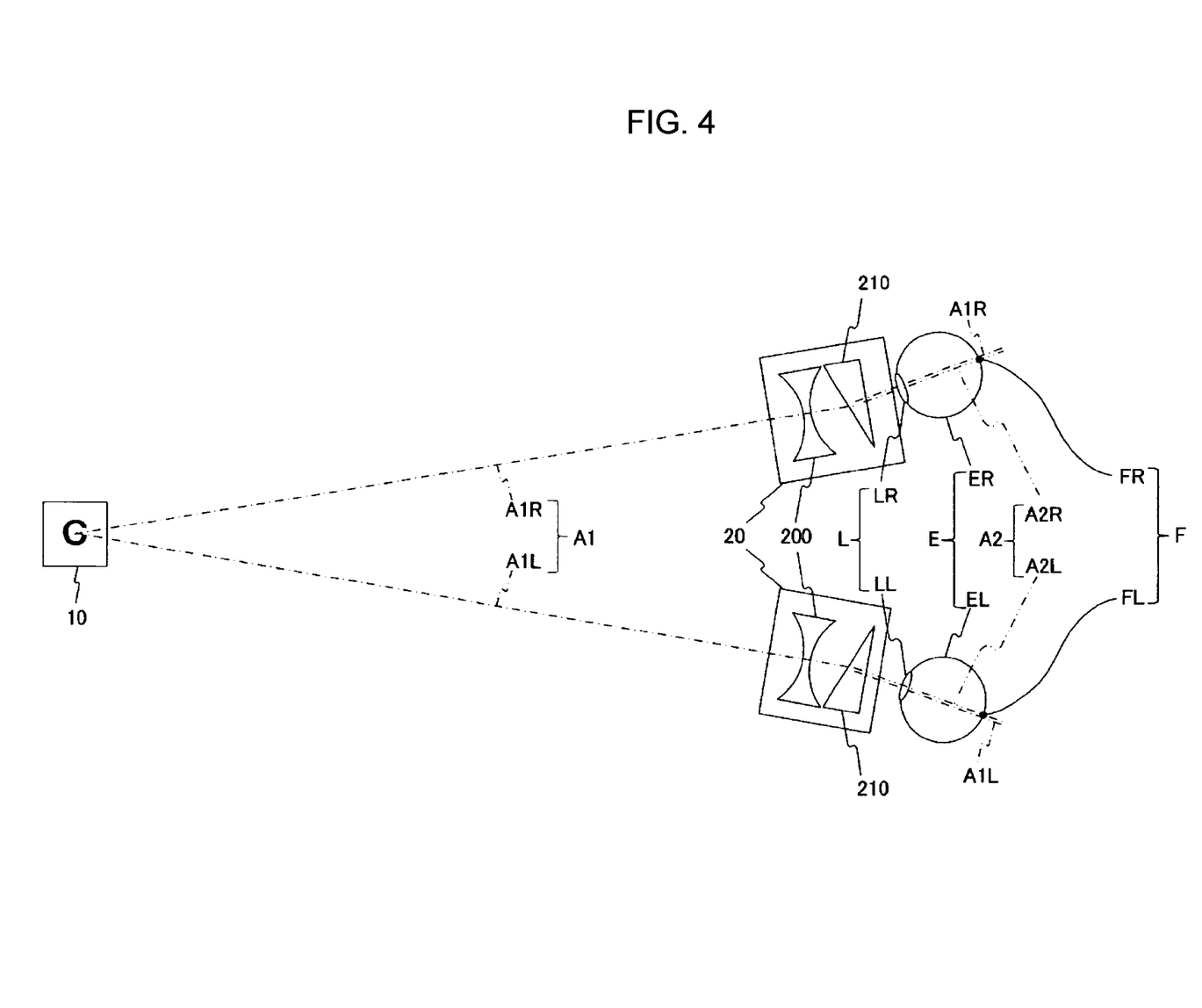
FIG. 4 is a schematic diagram illustrating an outline of a subjective optomater according to an embodiment.

FIG. 1 is a block diagram illustrating a configuration of a subjective optometer according to the present embodiment. FIG. 2 is a schematic diagram illustrating a state in which eyes E (a left eye EL and a right eye ER) visually recognize a visual target 10 through a measuring optical system 20. FIG. 3 is a schematic diagram illustrating a state in which visual axes converge. FIG. 4 is a schematic diagram illustrating a state in which measuring optical axes are aligned with the visual axes. Although the measuring optical axes that have been aligned with the visual axes are illustrated at a position displaced from the visual axes in FIG. 4, the measuring optical axes and the visual axes are assumed to be aligned with each other optically.

The subjective optometer 1 includes the visual target 10, the measuring optical system 20, a spherical power changer 30, a deflection controller 40, a controller 50 and an operation part 60.

(Visual Target 10)

The visual target 10 is presented to the eyes E through measuring optical axes A1 (a measuring optical axis A1L for a left eye and a measuring optical axis A1R for a right eye). A subject visually recognizes the visual target 10 a predetermined distance away and answers how it is seen. The measuring optical axes A1 express optical axes for causing the eyes E to visually recognize the visual target 10, that is, centers of optical paths through which light from the visual target is guided to the eyes E. The visual target 10 is presented to the eyes by a display device such as liquid crystal display, for example. Alternatively, the visual target 10 may be presented to the eyes by information printed on a paper.

(Measuring Optical System 20)

The measuring optical system 20 refracts light from the visual target 10. The measuring optical system 20 includes a spherical lens 200 and an optical axis deflector 210. The spherical lens 200 induces accommodation ability of the eyes E. Specifically, upon receiving influence from the spherical lens 200, the eyes E carry out accommodation to thicken a crystalline lens and try to see the visual target 10 clearly. The spherical lens 200 is configured to be capable of changing spherical power on the measuring optical axes A1. This configuration may be a configuration in which a plurality of spherical lenses 200 having different spherical powers are removably inserted into the measuring optical axes A1, for example.

The optical axis deflector 210 includes a prism lens that deflects so as to align the measuring optical axes A1 with visual axes A2 (a visual axis A2L of the left eye and a visual axis A2R of the right eye). The visual axes A2 are axes passing through centers of crystalline lenses L (a crystalline lens LL of the left eye and a crystalline lens LR of the right eye) and central foveas F (a central fovea FL of the left eye and a central fovea FR of the right eye). The prism lens is configured to be capable of changing the amount of prism on the measuring optical axes A1. This configuration may be a configuration in which a plurality of prism lenses having different amounts of prism are removably inserted into the measuring optical axes A1, for example.

(Spherical Power Changer 30)

The spherical power changer 30 changes the spherical power of the spherical lens 200. For example, when an operator selects predetermined spherical power by using the operation part 60, it may be configured that the controller 50 controls the spherical power changer 30 to change the spherical power of the spherical lens 200 to the selected spherical power. The spherical power changer 30 stores the spherical powers of the spherical lenses 200 on the measuring optical axes A1.

(Deflection Controller 40)

The deflection controller 40 finds the deflection angles of the measuring optical axes A1 based on the spherical powers of the spherical lenses 200 and selects prism lenses corresponding to these deflection angles. The deflection angles are angles of refracting the measuring optical axes A1 by the optical axis deflector 210 so as to align the measuring optical axes A1 with the visual axes A2. The deflection controller 40 previously stores relation information that relates selectable prism lenses and amounts of prism thereof. The deflection controller 40 obtains the spherical powers of the spherical lenses 200 on the measuring optical axes A1 upon receiving output from the spherical power changer 30.

As described above, influence from spherical lens causes accommodation of human eyes and this accommodation causes convergence of the visual axes A2. The amount of convergence of such accommodative convergence corresponds to misregistration between the measuring optical axes A1 and the visual axes A2 and is expressed as the deflection angles. Therefore, when accommodative convergence occurs, the measuring optical axes A1 are deflected by angles corresponding to the deflection angles so as to align the measuring optical axes A1 with the visual axes A2.

Regarding accommodative convergence, it is known as a clinically standard value that convergence of visual axes of 4Δ (4 prism-diopter) in both eyes is caused when crystalline lenses of human eyes are accommodated by 1D (1 diopter). Consequently, the relationship between spherical powers of spherical lenses and amounts of convergence of eyes are expressed as the following equation.

$$P1 = D1 \times 4 \qquad \text{[Equation 1]}$$

P1: amount of convergence in both eyes [Δ]
D1: spherical power of spherical lens [D]

For example, if the spherical power of a spherical lens is −0.25 D, the amount of convergence of the visual axes A2 of both eyes becomes 1Δ. In this case, the deflection controller 40 obtains 0.5ΔBO for the respective eyes (that is, 1Δ-divergence in both eyes) as deflection angles, and selects prism lenses having closest prism amount to the obtained deflection angles based on the relation information for the optical axis deflector 210. Since the optical axis deflector 210 aligns the measuring optical axes A1 with the visual axes A2, the eyes can fuse the visual target. In this way, the deflection controller 40 obtains deflection angles of the measuring optical axes A1 based on the spherical power of the spherical lens 200, and selects prism lenses based on the deflection angles obtained. It should be noted that if AC/A ratio has been measured for a subject, the deflection controller 40 may select prism lenses based on the AC/A ratio of the subject instead of the clinically standard value.

Alternatively, the operator may select desired prism lenses via the operation part 60 and the controller 50. When the operator selects desired prism lenses, a display 70 may receive output from the spherical power changer 30 and the controller 50 and display the spherical power of the concerned spherical lens.

(Controller 50, Operation Part 60 and Display 70)

The controller 50 controls operations of the respective parts. The controller 50 includes a processor and storage, for example. The processor may be CPU (Central Processing Unit), GPU (Graphic Processing Unit) or ASIC (Application Specific Integrated Circuit), for example. The storage includes ROM (Read Only Memory), RAM (Random Access Memory) and HDD (Hard Disc Drive), for example. The storage stores computer programs for executing functions of the respective parts of the subjective optometer 1. The processor executes these computer programs to realize the abovementioned control processing. The operation part 60 is used by the operator for manipulating the subjective optometer 1. The operation part 60 includes various hardware keys (buttons, switches, etc.) provided on a case of the subjective optometer 1 and the like. In a case in which a touch panel display and/or GUI are/is provided, various software keys displayed on them are included in the operation part 60. The display 70 displays information such as spherical powers of the spherical lens 200 and prism amounts of prism lenses. The display 70 is configured by a display device such as a liquid crystal display.

[Operation]

Figure 5:
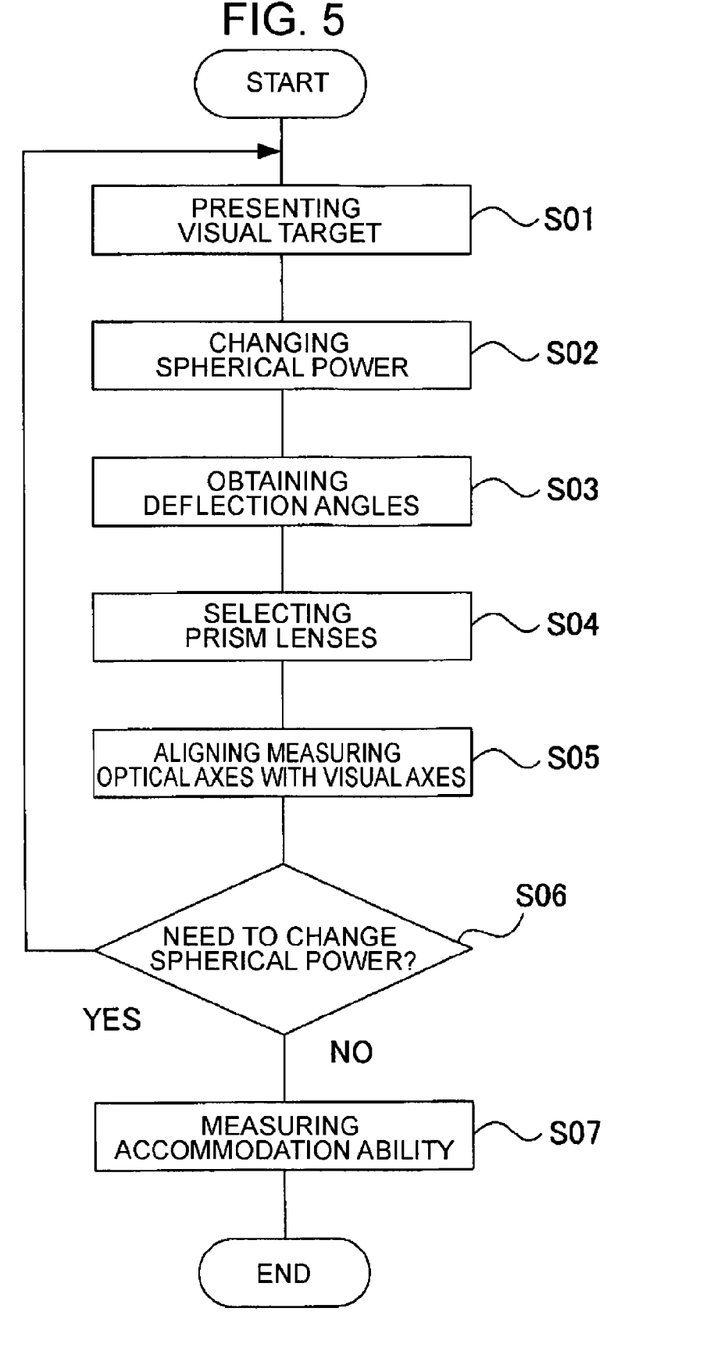
FIG. 5 is a flowchart illustrating an example of operation of a subjective optomater according to an embodiment.

Operations of a subjective optometer of the present embodiment are explained with referring to FIG. 5. FIG. 5 is a flow chart showing an operation of the subjective optometer 1.

(S01)

The controller 50 controls the visual target 10 to present the visual target 10 to the eyes through the measuring optical axes A1.

(S02)

The controller 50 controls the spherical power changer 30 to change the spherical power of the spherical lens 200.

(S03)

The controller 50 controls the deflection controller 40 to obtain deflection angles of the measuring optical axes A1 based on the spherical power of the spherical lens 200.

(S04)

The controller 50 controls the deflection controller 40 to select prism lenses corresponding to the deflection angles obtained.

(S05)

The measuring optical axes A1 are aligned with the visual axes A2 as a result of the selection of prism lenses by the deflection controller 40.

(S06, S07)

If it is necessary to change the spherical power of the spherical lens 200 further, the controller 50 executes the operation of Step S02. If it is not necessary to change the spherical power of the spherical lens 200 further, the subjective optometer 1 measures accommodation ability of the eyes based on the spherical power of the spherical lens 200.

[Actions and Effects]

The actions and effects of the present embodiment are explained.

The subjective optometer 1 includes the visual target 10, the measuring optical system 20, the spherical power changer 30 and the optical axis deflector 210. The visual target 10 is presented to the eyes E through the measuring optical axes A1. The measuring optical system 20 includes the spherical lens 200 that is capable of changing spherical power. The spherical power changer 30 changes the spherical power of the spherical lens 200. The optical axis deflector 210 deflects the measuring optical axes A1 so as to align the measuring optical axes A1 with the visual axes A2 of the eyes E. The optical axis deflector 210 may be a prism lens that deflects the measuring optical axes A1 so as to align the measuring optical axes A1 with the visual axes A2. The subjective optometer 1 may further include the deflection controller 40. The deflection controller 40 obtains deflection angles of the measuring optical axes A1 base on the spherical power of the spherical lens 200, and selects prism lenses corresponding to these deflection angles. Therefore, the subjective optometer 1 measures accommodation ability based on the spherical power of the spherical lens 200 in a state in which the measuring optical axes A1 are deflected by the optical axis deflector 210. In this manner, the subjective optometer 1 is capable of measuring accommodation ability of the eyes E in a state in which the measuring optical axes A1 are aligned with the visual axes A2, that is, in a state in which the eyes fuse the visual target 10. Consequently, it is possible to provide a subjective optometer that is capable of measuring accommodation ability of the eyes E while reducing the influence of accommodative convergence.

Second Embodiment

Figure 6:
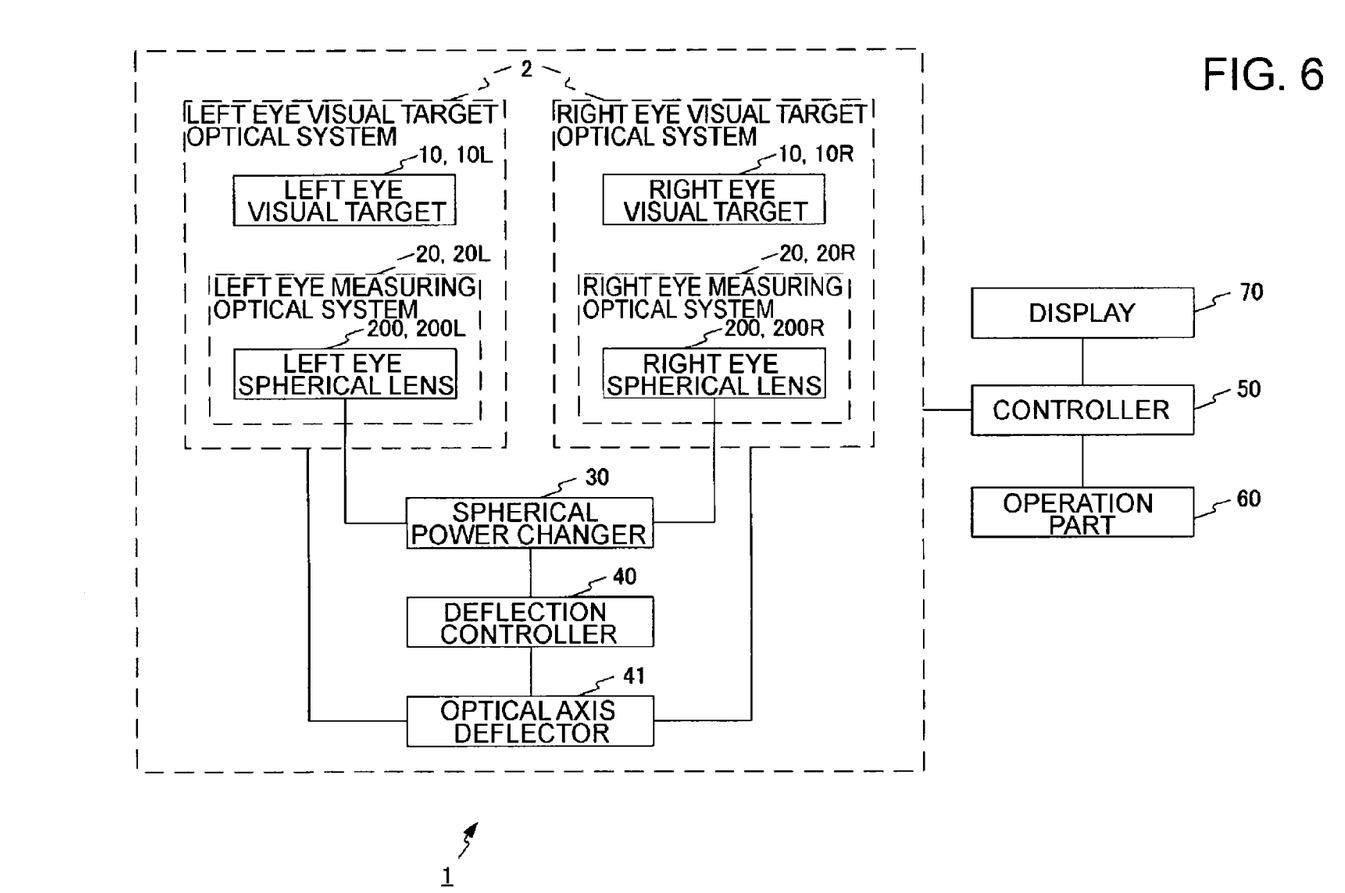
FIG. 6 is a block diagram illustrating an example of a configuration of a subjective optomater according to an embodiment.
Figure 7:
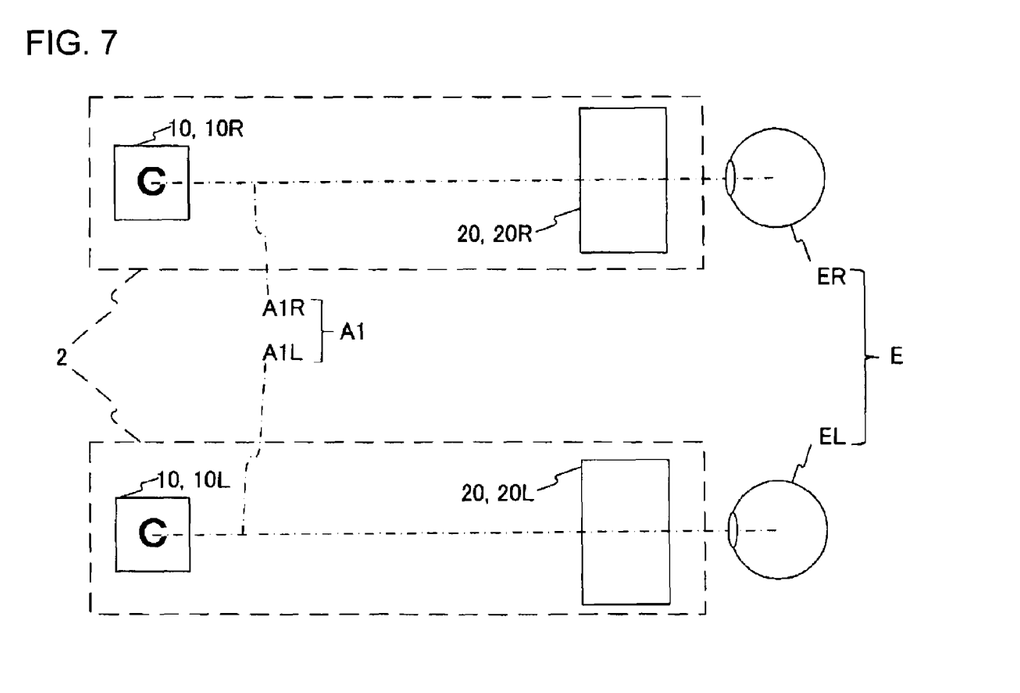
FIG. 7 is a schematic diagram illustrating an outline of a subjective optomater according to an embodiment.
Figure 8:
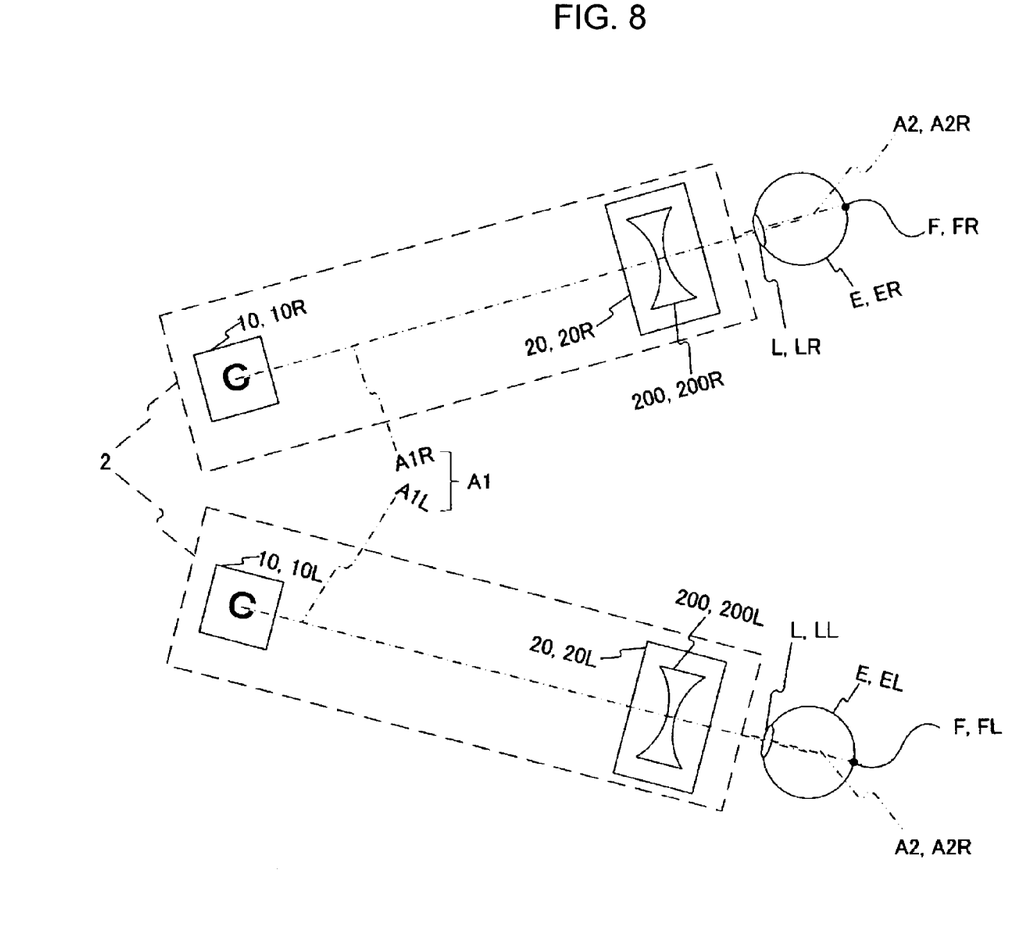
FIG. 8 is a schematic diagram illustrating an outline of a subjective optomater according to an embodiment.

FIG. 6 is a block diagram illustrating a configuration of a subjective optometer according to the present embodiment. Configurations of a visual target, measuring optical system and optical axis deflector of the present embodiment are different from those of the first embodiment. Other configurations are similar to those of the first embodiment. FIG. 7 is a schematic diagram illustrating a state in which the eyes E (a left eye EL and a right eye ER) visually recognize the visual target 10 through the measuring optical system 20. FIG. 8 is a schematic diagram illustrating a state in which the measuring optical axes are aligned with the visual axes. Although the measuring optical axes that have been aligned with the visual axes are illustrated at a position displaced from the visual axes in FIG. 8, the measuring optical axes and the visual axes are assumed to be aligned with each other optically.

The subjective optometer 1 includes a visual target optical system 2 the visual target 10 (a left eye visual target 10L and a right eye visual target 10R) and the measuring optical system 20 (left eye measuring optical system 20L and a right eye measuring optical system 20R) are integrally configured in the visual target optical system 2 for each of the left eye EL and the right eye ER, and the visual target optical system 2 is capable of being driven. The measuring optical system 20 includes the spherical lens 200 (a left eye spherical lens 200L and a right eye spherical lens 200R) that is capable of changing spherical power on the measuring optical axis A1. The left eye visual target 10L and the left eye visual target 10R are indicators presented only to the left eye EL and the right eye ER, respectively. The visual target optical system 2 generates distance between the visual target 10 and the eyes E in an optical way. The visual target optical system may be configured by applying a general optical-device configuration of an optometer in which visual targets are equipped for left eye and right eye independently.

An optical axis deflector 41 deflects the measuring optical axes A1 so as to align the measuring optical axes A1 with the visual axes A2 of the eyes E. Further, the optical axis deflector 41 is a driver that drives the target optical system 2. This driver may be configured by general mechanisms such as motors and gears.

The deflection controller 40 finds the deflection angles of the measuring optical axes based on the spherical powers of the spherical lenses 200 and drives the target optical system 2 based on these deflection angles. The deflection controller 40 receives output from the spherical power changer 30 and obtains the spherical powers of the spherical lenses 200 on the measuring optical axes A1.

Calculation of driving amount in this driving operation is explained by using clinically standard values of amounts of accommodative convergence of human eyes described above. The relationship between spherical powers of the spherical lens 200 and amounts of convergence of the visual axes A2 is expressed by the [Equation 1] described above. Further, prism amount 1Δ is an amount that displaces an image positioned 1 meter away by 1 centimeter. Therefore, deflection angles of the measuring optical axes A1 are expressed by the following equation.

$$R1 = \tan^{-1}[(P1/2)/100]$$

$$P1 = D1 \times 4 \quad \text{[Equation 2]}$$

R1: deflection angle of measuring optical axes [rad]
P1: amount of convergence in both eyes [Δ]
D1: spherical power of spherical lens [D]

For example, if the spherical power of the spherical lens 200 is −1D, the deflection angle of the measuring optical axes A1 becomes 0.02 rad. In this case, the optical axis deflector 41 calculates 0.02 rad as driving amount for the respective eyes, and the optical axis deflector 41 drives the target optical system 2. From this driving operation, the measuring optical axes A1 are aligned with the visual axes A2. It should be noted that if AC/A ratio has been measured for a subject, the optical axis deflector 41 may determine the amount of convergence of the target optical system 2 by using the AC/A ratio of the subject instead of the clinically standard value.

Further, the operator may select a desired driving amount via the operation part 60 and the controller 50. When the operator selects the desired driving amount, the display 70 may receive output from the spherical power changer 30 and the controller 50 and display the spherical power of the concerned spherical lens.

[Operation]

Figure 9:
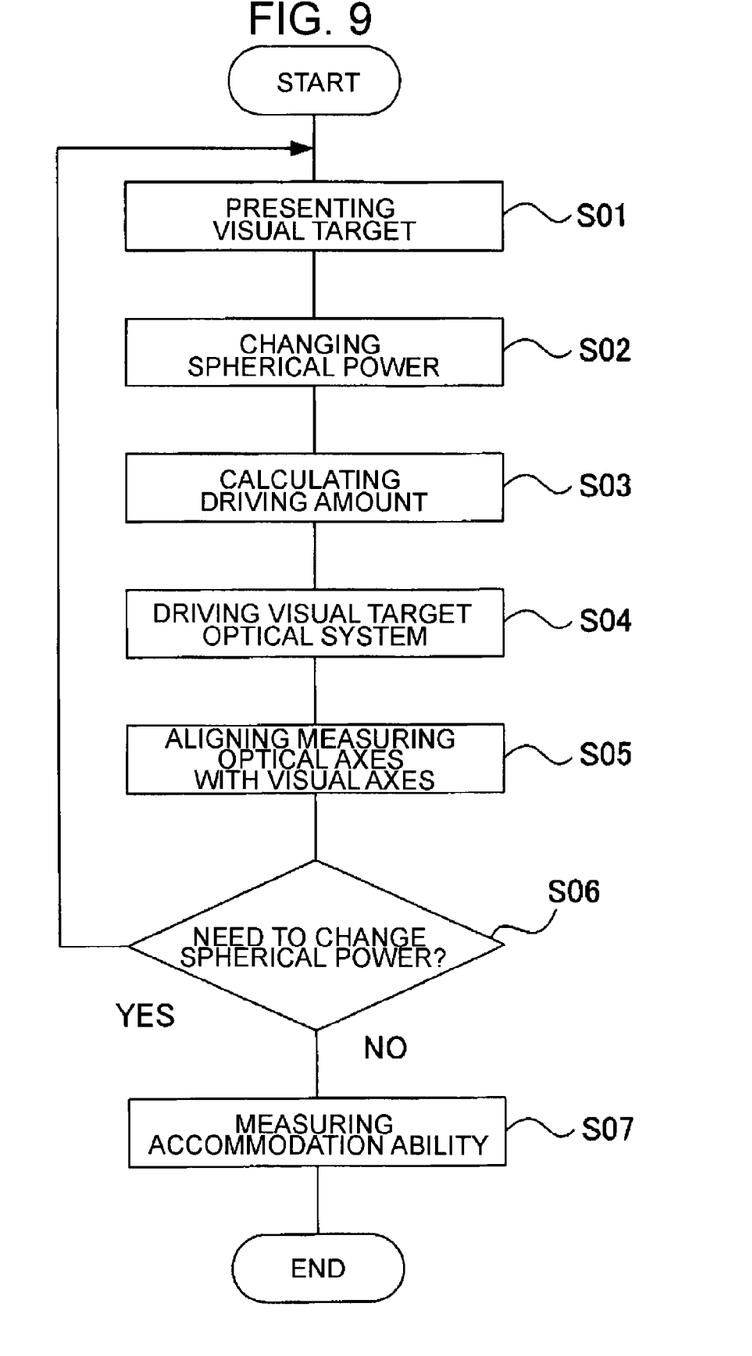
FIG. 9 is a flowchart illustrating an example of operation of a subjective optomater according to an embodiment.

Operations of a subjective optometer of the present embodiment are explained with referring to FIG. 9. FIG. 9 is a flow chart showing an operation of the subjective optometer 1.

(S01)

The controller 50 controls the visual target 10 to present the visual target 10 to the eyes through the measuring optical axes A1.

(S02)

The controller 50 controls the spherical power changer 30 to change the spherical power of the spherical lens 200.

(S03)

The controller 50 controls the deflection controller 40 to obtain deflection angles of the measuring optical axes A1 based on the spherical power of the spherical lens 200.

(S04)

The controller 50 controls the deflection controller 40 to cause the optical axis deflector 41 to drive the target optical system 2.

(S05)

The measuring optical axes A1 are aligned with the visual axes A2 as a result of the operation of driving the target optical system 2 performed by the optical axis deflector 41.

(S06, S07)

If it is necessary to change the spherical power of the spherical lens 200 further, the controller 50 executes the operation of Step S02. If it is not necessary to change the spherical power of the spherical lens 200 further, the subjective optometer 1 measures accommodation ability of the eyes based on the spherical power of the spherical lens 200.

[Actions and Effects]

The actions and effects of the present embodiment are explained.

The subjective optometer 1 includes the visual target optical system 2, the spherical power changer 30 and the optical axis deflector 41. The visual target optical system 2 includes the visual target 10 and the measuring optical system 20 that are integrally configured for each of the left eye EL and the right eye ER. The visual target optical system 2 optically generates distance between the visual target 10 and the eyes E for the respective left and right eyes. The visual target 10 is presented to the eyes E through the measuring optical axes A1. The measuring optical system 20 includes the spherical lens 200 that is capable of changing spherical power. The spherical power changer 30 changes the spherical power of the spherical lens 200. The optical axis deflector 41 deflects the measuring optical axes A1 so as to align the measuring optical axes A1 with the visual axes A2 of the eyes E. Further, the optical axis deflector 41 may be a driver that drives the visual target optical system 2. The subjective optometer 1 may further include the deflection controller 40. The deflection controller 40 obtains deflection angles of the measuring optical axes A1 base on the spherical power of the spherical lens 200, and causes the optical axis deflector to drive the visual target optical system based on these deflection angles. Therefore, the subjective optometer 1 measures accommodation ability based on the spherical power of the spherical lens 200 in a state in which the measuring optical axes A1 are deflected by the optical axis deflector 41. In this manner, the subjective optometer 1 is capable of measuring accommodation ability of the eyes E in a state in which the measuring optical axes A1 are aligned with the visual axes A2, that is, in a state in which the eyes fuse the visual target 10. Consequently, it is possible to provide a subjective optomater that is capable of measuring accommodation ability of the eyes E while reducing the influence of accommodative convergence.

While certain embodiments have been described, these embodiments have been presented by way of example only, and are not intended to limit the scope of the inventions. The embodiments described herein may be embodied in a variety of other forms; furthermore, various omissions, substitutions and changes in the form of the embodiments described herein may be made without departing from the spirit of the invention. The accompanying claims and their equivalents are intended to cover such forms or modifications as would fall within the scope and spirit of the invention.

EXPLANATION OF SYMBOLS 1 subjective optometer
2 visual target optical system
10 visual target
10L left eye visual target
10R right eye visual target
20 measuring optical system
20L left eye measuring optical system
20R right eye measuring optical system
30 spherical power changer
40 deflection controller
41 optical axis deflector
50 controller
60 operation part
70 display
200 spherical lens
200L left eye spherical lens 200R right eye spherical lens
210 optical axis deflector
A1 measuring optical axes
A1L measuring optical axis
A1R measuring optical axis
A2 visual axes
A2L visual axis
A2R visual axis
E eyes
EL left eye
ER right eye
F central foveas
FL central fovea
FR central fovea
L crystalline lenses
LL crystalline lens
LR crystalline lens

What is claimed is:

1. A subjective optometer comprising:
    a visual target that is presented to an eye through a measuring optical axis;
    a measuring optical system that includes a spherical lens capable of changing spherical power on the measuring optical axis;
    a spherical power changer that changes the spherical power of the spherical lens; and
    an optical axis deflector that deflects the measuring optical axis so as to align the measuring optical axis with a visual axis of the eye,
    wherein accommodation ability is measured based on the spherical power of the spherical lens in a state in which the measuring optical axis is deflected by the optical axis deflector.

2. The subjective optometer of claim 1, wherein the optical axis deflector includes prism lenses that deflects the measuring optical axis to align the measuring optical axis with the visual axis.

3. The subjective optometer of claim 2, further comprising a deflection controller that obtains a deflection angle of the measuring optical axis based on the spherical power of the spherical lens and selects a prism lens corresponding to the deflection angle obtained.

4. The subjective optometer of claim 1, comprising a visual target optical system for each of a right and left eyes in which the visual target and the measuring optical system are integrally configured, wherein the visual target optical system is capable of being driven,
    wherein the optical axis deflector includes a driver that drives the visual target optical system.

5. The subjective optometer of claim 4, further comprising a deflection controller that obtains a deflection angle of the measuring optical axis based on the spherical power of the spherical lens and controls the optical axis deflector to drive the visual target optical system based on the deflection angle obtained.

* * * * *